United States Patent
Mizobuchi et al.

(10) Patent No.: US 7,029,663 B1
(45) Date of Patent: Apr. 18, 2006

(54) STABLE OINTMENT CONTAINING ACETYLSALICYLIC ACID

(75) Inventors: Noriko Mizobuchi, Kochi (JP); Yuichi Hasegawa, Kakogawa (JP); Mitsuhiro Kawada, Kagawa-ken (JP); Shin-ichi Hisaichi, Kagawa-ken (JP)

(73) Assignee: Teikoku Seiyaku Co., Ltd., Ohkawa-gun (JP)

( * ) Notice: Subject to any disclaimer, the term of this patent is extended or adjusted under 35 U.S.C. 154(b) by 577 days.

(21) Appl. No.: 09/242,700

(22) PCT Filed: Jun. 23, 1998

(86) PCT No.: PCT/JP98/02781

§ 371 (c)(1),
(2), (4) Date: Apr. 19, 1999

(87) PCT Pub. No.: WO98/58652

PCT Pub. Date: Dec. 30, 1998

(30) Foreign Application Priority Data

Jun. 25, 1997 (JP) .................................. 9-168513

(51) Int. Cl.
  A61K 31/74 (2006.01)
  A61K 9/00 (2006.01)
  A01N 37/36 (2006.01)

(52) U.S. Cl. ................ 424/78.05; 424/400; 424/78.02; 514/165; 514/887; 514/944; 514/947

(58) Field of Classification Search ................ 514/944, 514/938, 887, 947, 165; 424/78.05, 400, 424/401, 78.02, 78.07
See application file for complete search history.

(56) References Cited

U.S. PATENT DOCUMENTS 4,012,508 A * 3/1977 Burton ........................ 424/235
4,164,563 A * 8/1979 Chang ........................ 514/10
4,228,162 A    10/1980 Luzzi et al.
4,613,498 A    9/1986 Crosby
4,665,063 A    5/1987 Bar-Shalom
4,686,212 A    8/1987 Ducatman et al.
4,794,107 A * 12/1988 Takashima et al. ......... 514/179
5,916,918 A *  6/1999 Konishi et al. ............. 514/546

FOREIGN PATENT DOCUMENTS

| GB | 469526 | | 7/1937 |
| GB | 2144326 | | 3/1985 |
| GB | 2144326 A | * | 3/1985 |
| GB | 2144326 | * | 3/1996 |
| JP | 5632425 | | 4/1981 |
| JP | 6289619 | | 4/1987 |
| JP | 62267232 A | * | 11/1987 |
| JP | 372426 | | 3/1991 |
| JP | 03072426 | * | 3/1991 |
| JP | 4346930 | | 12/1992 |
| JP | 5246892 | | 9/1993 |
| JP | 672879 | | 3/1994 |
| JP | 6183980 | | 7/1994 |
| JP | 8113531 | | 5/1996 |
| JP | 8208487 | | 8/1996 |
| JP | 9235232 | | 9/1997 |

OTHER PUBLICATIONS

Journal of the Nippon Hospital Pharmacists Association, vol. 20, No. 6 (1994), p. 502-508.
Pharmaceutics, Published by the Press of Human Hygiene, 3rd Ed., Edited by Xi, Nian Zhu, pp. 376-377, (1995) with an English translation thereof.

* cited by examiner

Primary Examiner—Sreeni Padmanabhan
Assistant Examiner—Sharmila S. Gollamudi
(74) Attorney, Agent, or Firm—Birch, Stewart, Kolasch & Birch, LLP

(57) ABSTRACT

A substantially anhydrous stable ointment containing Aspirin which is characterized in using gelation hydrocarbon and/or vaseline as a base. The ointment is superior in stability and can be stored for a long term.

5 Claims, No Drawings

STABLE OINTMENT CONTAINING ACETYLSALICYLIC ACID

This application is the national phase under 35 U.S.C. §371 of prior PCT International Application No. PCT/JP98/02781 which has an International filing date of Jun. 23, 1998 which designated the United States of America.

TECHNICAL FIELD

The present invention relates to a stable ointment containing Aspirin (acetyl salicylic acid).

More specifically, the present invention relates to a substantially anhydrous ointment containing Aspirin characterized in using hydrocarbon gel and/or vaseline (petrolatum) as a base, which can preserve Aspirin stably for a long term.

BACKGROUND ART

Aspirin has been used as anti-inflammatoric antipyretic analgesics from of old. It is in general orally administered in form of tablets, granules and so on.

However, due to the intestinal injury by Aspirin, its external application has been recently studied and it has been done to try to make it percutaneously absorb. The results are reported in Japanese Patent Pub. No. 3-72426 in form of ointments for treatment of neuralgia, in Japanese Patent Pub. No. 6-72879 in form of patches containing Aspirin, in Japanese Patent Pub. No. 6-183980 as a stabilizing method of Aspirin in patches containing it. Further, patches containing Aspirin are disclosed in Japanese Patent Pub. No. 8-113531. Techniques such as improvement of transdermal absorption of Aspirin and stabilization of it in plasters are mainly disclosed in these publications. However, any technique to maintain Aspirin stably in ointments for a long term is not disclosed.

The literatures which describe methods for stabilization of Aspirin in preparations except for external preparations, are Japanese Patent Pub. No. 56-32425, Japanese Patent Pub. No. 62-89619, Japanese Patent Pub. No. 4-346930 and so on.

Because Aspirin is readily hydrolyzed even in the presence of small amount of water and furthermore, by depending on a kind of additives the hydrolysis is accelerated, in these literatures in order to avoid to contact with the additive, it is disclosed to use the protective layer consisting of sucrose, or to use binders in which water was excluded as much as possible degree and to add a hydrogenated oil as a lubricant. However, it is hardly possible to apply such techniques to ointments.

As such, in external preparations of Aspirin, the technique to secure the stability of Aspirin in preparing ointments has not been shown.

DISCLOSURE OF INVENTION

The present invention was made considering the above problems and the object of the present invention is to provide ointments containing Aspirin which are superior in stability and can be stored for a long term.

That is, by preparing substantially water free-ointments prepared by adding Aspirin to a base comprising hydrocarbon gel and/or vaseline (petrolatum) it was found to solve the above problems and thus the present invention was completed.

Hydrocarbon gel and vaseline in the present invention are used in substantially anhydrous state. Vaseline is one ordinary used as a base for preparation of ointments, such as yellow vaseline, white vaseline and their mixture.

The amount of Aspirin in an ointment of the present invention is 0.001 to 30% by weight, preferably 0.01 to 20% by weight, more preferably 0.05 to 15% by weight. In case of more than 30% by weight of Aspirin, it is impossible to maintain the property of ointments and in addition the protection effect by the base decreases to cause hydrolysis of Aspirin. On the other hand, in case of less than 0.001% by weight of Aspirin it is hardly to exhibit the pharmacological activities of Aspirin. Either case is not preferable.

The ointments of the present invention containing Aspirin are prepared by the same method as ordinary ointments. That is, after melting a base by warming, thereto fine powders of Aspirin are added under stirring and mixed to prepare ointments.

In case of preparation of these ointments, to add water in order to dissolve Aspirin and the like is not preferable and should be avoided.

Furthermore, it is not preferable to add any additive which destroys stability of Aspirin, such as an organic acid, an alcohol, a polyhydric alcohol, a surfactant, etc.

BEST MODE FOR CARRYING OUT THE INVENTION

The present invention is shown in more detail by the following examples. But the present invention is not limited by the examples.

EXAMPLE 1

According to the following ingredients, white vaseline was put in a vacuum emulsifier (T.K.ROBO MIXER prepared by Tokusyukika Kogyo) to be melted under heating at 55° C. Thereto Aspirin was added and the mixture was stirred under vacuum at 2,000 rpm for 15 minutes. Then the mixture was cooled to 25° C. to give ointments containing Aspirin.

| Ingredients | Contents |
|---|---|
| Aspirin | 0.5 g |
| White vaseline | 99.5 g |

EXAMPLE 2

According to the following ingredients, yellow vaseline and Aspirin were put in a grinder and the mixture was stirred at 100 rpm to give ointments containing Aspirin.

| Ingredients | Contents |
|---|---|
| Aspirin | 8.0 g |
| Yellow vaseline | 92.0 g |

EXAMPLE 3

According to the following ingredients, hydrocarbon gel and Aspirin were put in a grinder and the mixture was stirred at 80 rpm to give ointments containing Aspirin.

| Ingredients | Contents |
|---|---|
| Aspirin | 5.0 g |
| Hydrocarbon gel (Japanese Pharmaceutical Excipients) | 99.5 g |

EXAMPLE 4

According to the following ingredients, hydrocarbon gel and Aspirin were put in a planetary mixer and the mixture was stirred under vacuum at 130 rpm for 20 minutes to give ointments containing Aspirin.

| Ingredients | Contents |
|---|---|
| Aspirin | 25.0 g |
| Hydrocarbon gel (Japanese Pharmaceutical Excipients) | 75.0 g |

EXAMPLE 5

According to the following ingredients and the method described in Example 4, there were obtained ointments containing Aspirin.

| Ingredients | Contents |
|---|---|
| Aspirin | 0.5 g |
| Hydrocarbon gel (Japanese Pharmaceutical Excipients) | 99.5 g |

EXAMPLE 6

According to the following ingredients and the method described in Example 4, there were obtained ointments containing Aspirin.

| Ingredients | Contents |
|---|---|
| Aspirin | 1.0 g |
| Hydrocarbon gel (Japanese Pharmaceutical Excipients) | 79.0 g |
| White vaseline | 20.0 g |

COMPARATIVE EXAMPLE 1

According to the following ingredients, polyacrylic acid was added to propylene glycol and the mixture was melted by warming on a water bath and stirred. Then, Aspirin was dissolved in the mixture and thereto triethanolamine was added. The mixture was stirred to give gelation ointments.

| Ingredients | Contents |
|---|---|
| Aspirin | 0.5 g |
| Polyacrylic acid | 0.5 g |
| Propylene glycol | 45.0 g |
| Triethanolamine | 0.67 g |
| Purified water | residual |
| Total | 100.0 g |

COMPARATIVE EXAMPLE 2

According to the following ingredients, carboxymethyl cellulose sodium was dispersed in ethanol. The mixture was added to a mixture of glycerin and propylene glycol under stirring. Then, Aspirin was dispersed and dissolved in the mixture. Thereto purified water was added and the mixture was stirred thoroughly to give gelation ointments.

| Ingredients | Contents |
|---|---|
| Aspirin | 0.5 g |
| Carboxymethyl cellulose sodium | 6.0 g |
| Ethanol | 8.0 g |
| Glycerin | 20.0 g |
| Propylene glycol | 20.0 g |
| Purified water | residual |
| Total | 100.0 g |

COMPARATIVE EXAMPLE 3

According to the following ingredients, hydrophilic ointments described in the Pharmacopeia of Japan XIII was prepared and thereto Aspirin was mixed to prepare a ointment.

| Ingredient of hydrophilic ointment | |
|---|---|
| White vaseline | 25.0 g |
| Stearyl alcohol | 20.0 g |
| Propylene glycol | 12.0 g |
| Polyoxyethylene hyroganated castor oil | 4.0 g |
| Glycerol monostearate | 1.0 g |
| p-Hydoxybenzoic acid methyl ester | 0.1 g |
| p-Hydoxybenzoic acid propyl ester | 0.1 g |
| Purified water | residual |
| Total | 100.0 g |

| Ingredients of ointment containing Aspirin | |
|---|---|
| Aspirin | 0.5 g |
| Hydrophilic ointment | 99.5 g |

Experiment 1

Ointments of the present invention prepared by Examples 1 and 5, and ointments prepared by Comparative Examples 1 to 4 were tested on stability in strage at 75% RH at 40° C., and at 50° C. Test samples were stored under each condition for one or two months, and after sampling, contents of Aspirin remaining in each sample were measured and the remaining percentage per initial contents was calculated and shown in Table 1.

Experiment 2

Ointments of the present invention prepared by examples 1 to 5 and ointments prepared by Comparative Example 1 were measured on the water contents in the by Karl-Fischer moisture content meter and the results were shown in Table 2.

TABLE 1

Test result on the stability of ointments containing Aspirin

| | 75% RH at 40° C. remain (%) | | | | at 50° C. remain (%) | | | |
|---|---|---|---|---|---|---|---|---|
| | Initial | 1 | 2 | 10.5 | Initial | 1 | 2 | 10.5 |
| Example 1 | 100 | 100.6 | 1002.4 | 96.9 | 100 | 96.0 | 97.8 | 91.7 |
| Example 5 | 100 | 101.2 | 1002.4 | 96.4 | 100 | 100.0 | 99.4 | 93.2 |
| Comp. Ex. 1 | 1001 | 15.4 | 1.2 | 0 | 100 | 0.8 | | 0 |
| Comp. Ex. 2 | 100 | 13.8 | 1.4 | 0 | 100 | 0 | 0 | |
| Comp. Ex. 3 | 100 | 20.7 | 0.4 | 0 | 100 | 0 | 0 | |

TABLE 2

The result of measurement of water content in ointments containing Aspirin

| | Ex. 1 | Ex. 2 | Ex. 3 | Ex. 4 | Ex. 5 |
|---|---|---|---|---|---|
| water contents (%) | 0.0190 | 0.0261 | 0.0098 | 0.0127 | 0.0066 |

| | Com. Ex. 1 | Com. Ex. 2 | Com. Ex. 3 |
|---|---|---|---|
| water contents % | 55.2438 | 45.2190 | 38.0261 |

INDUSTRIAL APPLICABILITY

The ointments of the present invention containing Aspirin can be stored stably Aspirin for a long term in form of the substantially anhydrous ointment containing hydrocarbon gel and/or vaseline as a base.

The invention claimed is:

1. An ointment consisting of acetyl salicylic acid and a base selected from the group consisting of hydrocarbon gel, petrolatum and a mixture thereof without any other additive for said acetyl salicylic acid and wherein the ointment does not contain water for dissolving said acetyl salicylic acid,
    wherein when the base is hydrocarbon gel or a mixture of hydrocarbon gel and petrolatum, the acetyl salicylic acid is in a range of 20 to 30% by weight per total weight, and wherein when the base is petrolatum, the acetyl salicylic acid is in a range of 25 to 30% by weight per total weight.

2. The ointment of claim 1, wherein the ointment is an anhydrous ointment.

3. The ointment of claim 1, wherein the base is petrolatum.

4. The ointment of claim 3, wherein the petrolatum is selected from the group consisting of white petrolatum and yellow petrolatum.

5. The ointment of claim 1, wherein the base is hydrocarbon gel.

\* \* \* \* \*